(12) United States Patent
Kiso et al.

(10) Patent No.: US 6,620,424 B1
(45) Date of Patent: Sep. 16, 2003

(54) PROCESS FOR PRODUCING GLYCOLYTIC METABOLISM REGULATORS

(75) Inventors: Yoshinobu Kiso, Osaka (JP); Aki Kusumoto, Osaka (JP); Eisuke Furuya, Osaka (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/582,425

(22) PCT Filed: Oct. 25, 1999

(86) PCT No.: PCT/JP99/05873

§ 371 (c)(1),
(2), (4) Date: Jun. 26, 2000

(87) PCT Pub. No.: WO00/24422

PCT Pub. Date: May 4, 2000

(30) Foreign Application Priority Data

Oct. 27, 1998 (JP) .......................................... 10-305732

(51) Int. Cl.$^7$ .............................................. A61K 47/00
(52) U.S. Cl. ...................................... 424/439; 424/400
(58) Field of Search ................................. 426/400, 439, 426/78.01; 514/866, 909

(56) References Cited

U.S. PATENT DOCUMENTS 4,211,765 A * 7/1980 Johnson et al. ................ 424/78
5,145,865 A * 9/1992 Fujii et al. .................... 514/424

FOREIGN PATENT DOCUMENTS

| DE | 2558551 A1 | * | 7/1977 |
| DE | 2558551 | | 7/1997 |
| EP | 0319988 | | 6/1989 |
| JP | 05170734 A | * | 7/1993 |
| JP | 10-327805 | | 12/1998 |
| JP | 11-151068 | | 6/1999 |
| WO | WO 98/20124 | | 5/1998 |

OTHER PUBLICATIONS

Inoue et al. "Insulin–like effects of vanadate on rat liver 6–phosphofructo–2–kinase/fructose–2,6–biphosphatase mRNA and protein inductions in diabetic rats" Endocrine J. vol 41, No. 1, Feb. 1, 1994, pp. 75–82.

E. Furuya, Seikagaku (Biochemistry), vol. 54, No. 12, pp. 1311–1317.

Harada, Y. et al., " Inhibition of Fructose –6–Phosphate, 2–Kinase by N–Bromoacetylethanolamine Phosphate In Vitro and In Vivo", J. Biochem., 1997, vol. 121, No. 4, pp. 724–730.

E. Furuya et al, Proc. Natl. Acad. Sci. U.S., vol. 77,: An activation factor of liver phosphofructokinase pp. 5861–5864 (1980).

E.Van Schaftingen et al., Biochem. J., vol. 192, "Control of the 6–phosphate/fructose 1,6–bisphosphate cycle in isolated hepatocytes by glucose and glucagon" pp. 887–895 1980.

E.Furuya et al., Proc. Natl. Acad. Sci. U.S., vol. 79, Regulation of fructose–6–phosphate 2–kinase by phosphorylation and dephosphorylation: Possible mechanism for coordinated control of glycolysis and glycogenolysis, pp. 325–329 (1982).

K. Kaku et al., "Extrapancreatic effects of sulfonurea Drugs", Diabetes Research and Clinical Practice, 1995, 28 Suppl., S105 to S108, Full Text.

Shimamoto, G. et al., "Taurine catalbolism III. Evidence for the participation of the glyoxylate cycle", Biochim, Biophys, Acta, 1980, vol. 632, pp. 399–407 see introduction.

* cited by examiner

Primary Examiner—Thurman K. Page
Assistant Examiner—Liliana Di Nola-Boran
(74) Attorney, Agent, or Firm—Paul E. White, Jr.; Manelli Denison & Selter, PLLC

(57) ABSTRACT

A food or beverage containing an effective amount of a fructose-6-phosphate-2-kinase inhibitor which is safe and effective in vivo, such as itaconic acid, and a pharmaceutical composition containing the inhibitor as an active ingredient are disclosed. This food, beverage or pharmaceutical composition safely exerts an antiobesity, antidiabetic, and an antilipemic effect.

10 Claims, 11 Drawing Sheets

PROCESS FOR PRODUCING GLYCOLYTIC METABOLISM REGULATORS

TECHNICAL FIELD

This invention relates to foods or drugs which are characterized by containing fructose-6-phosphate-2-kinase inhibitors, such as itaconic acid and its salts, as active ingredients, and which exert antiobesity, antidiabetic, and antilipemic effects due to the existence of inhibitors that function to suppress the glycolytic pathway and the activity of phosphofructokinase, a regulatory enzyme of the glycolytic pathway. The invention also relates to a method for preparing these foods or drugs.

BACKGROUND ART

Obesity tends to cause such complications as hypertension, abnormal glucose tolerance, or hyperlipidemia, and is considered to be a risk factor in diseases such as ischemic heart disease, cerebral apoplexy, and diabetes. From the point of view of preventing such diseases, prevention of obesity is of vital importance.

Obesity refers to an excessive accumulation of fat in the body. This state occurs when regulatory function on energy balance becomes impaired, or when intake of energy exceeds consumption of energy over a long period beyond the range tolerable for the regulatory function. Thus, obesity is improved by rectifying the impaired regulatory function to normal, or by forcibly increasing energy consumption (exercising) and restricting energy intake (dieting), to create an energy deficient state whereby fat in the body is consumed. However, the conventionally adopted measures of regular exercise and controlled dieting in a busy daily life are often not adhered to by obesity sufferers. Therefore, a number of persons classified as obese tends to be increasing.

Impairment of the regulation of energy balance in the body for the reasons as outlined above—excessive energy intake versus consumption over a protracted period—can also lead to the development diseases such as diabetes and hyperlipidemia. As antidiabetic agents there are commercially available inhibitors of carbohydrate degradation enzymes, which inhibit the degradation or absorption of carbohydrates. However, administration of these enzymes can cause adverse reactions, such as hypoglycemia, loose stools or diarrhea, and therefore are required to be administered under management by physicians. Clofibrate-derived drugs and nicotinate drugs are used as antilipemic agents, but again, these drugs are required to be administered under management by physicians.

In the body, carbohydrates taken in from foods are first used for glycogen synthesis in the liver and muscles. Accumulated glycogen in the liver is used by the body to prevent decreases in fasting blood glucose. Excessive carbohydrate is metabolized by the hepatic glycolytic pathway and converted into acetyl-CoA. It is then available for use partially as an energy source, but is mostly utilized in the synthesis of fatty acids or lipids such as cholesterol.

The regulatory enzyme for glycolytic pathway metabolism in the liver is phosphofructokinase (PFK). This enzyme is inhibited by adenosine triphosphate (ATP), citric acid, and phosphoenolpyruvic acid (PEP), and activated by adenosine monophosphate (AMP) and fructose 6-phosphate (F6P). However, changes in the concentrations of these regulatory factors in the liver, unlike those in muscles, are not sufficient to account for changes in the activity of PFK. Thus, a problem existed in finding a satisfactory explanation of the regulation of hepatic PFK activity. Under these circumstances, a search for new regulatory factors for PFK was conducted, and in 1980, fructose 2,6-bisphosphate (F26BP) was isolated as the most potent activating factor (E. Furuya & K. Ueda, Proc., Natl. Acad. Sci. U.S., Vol. 77, 5861–5864, 1980; E. Van Schaftingen et al., Biochem. J., Vol. 192, 887–895 and 897–901, 1980).

F26BP is said to be a regulatory factor, rather than a mere activating factor for PFK because the intracellular concentration of F26BP rapidly changes with insulin or glucagon. F26BP is synthesized from F6P by the action of fructose-6-phosphate-2-kinase (F6P2kinase). F26BP is converted to F6P by the action of fructose 2,6-bisphosphatase (F26pase). These two enzyme activities are shouldered by a single enzyme protein (bifunctional enzyme). Dephosphorylation of this enzyme protein promotes activity of F6P2kinase, while phosphorylation of the enzyme protein promotes activity of F26Pase. Following the ingestion of carbohydrate, insulin is secreted by the pancreas. Protein phosphatase activated by insulin dephosphorylates the bifunctional enzyme to activate F6P2kinase, thereby increasing the concentration of F26BP. As a result, PFK is activated to promote metabolism of the glycolytic pathway. In a fasting state, on the other hand, the bifunctional enzyme is phosphorylated by the action of glucagon to activate F26Pase to decrease the concentration of F26BP. Thus, the activity of PFK declines, suppressing the metabolism of the glycolytic pathway (E. Furuya et al., Pro., Natl. Acad. Sci. U.S., Vol. 79, 325–329, 1982).

As described above, the fructose 6-phosphate-2-kinase:fructose 2,6-bisphosphatase bifunctional enzyme (F6P2kinase:F26Pase) undergoes regulation by phosphorylation with glucagon-activated cAMP-dependent protein kinase, and dephosphorylation with insulin-activated protein phosphatase. Its enzyme activities are also known to be affected by glycerol 3-phosphate (Glycerol 3-P), phosphoenolpyruvic acid (PEP), 3-phosphoglycerate (3-P-glycerate), and 2-phosphoglycerate (2-P-glycerate). These regulatory factors have been reported to inhibit F6P2kinase, promote F26Pase activity, and also promote phosphorylation of F6P2kinase:F26Pase (E. Van Schaftingen, Adv. Enzymol. Vol. 59, 315–395, 1987).

DISCLOSURE OF THE INVENTION

In view of the foregoing, there has been a demand for the development of foods, drinks, or drugs, which exert safely an antiobesity, antidiabetic, and antilipemic effect without involving distress.

The inventors of the present invention directed their attention to the regulation of the glycolytic pathway metabolism as a way of decreasing energy intake without reducing food intake. They searched for substances among food components active in inhibiting glycolytic pathway metabolic enzymes, which can be utilized safely and conveniently. As a result, they identified itaconic acid as one of the fructose 6-phosphate-2-kinase inhibitors which suppresses the activity of phosphofructokinase, a regulatory enzyme for glycolytic pathway metabolism. In animals administered itaconic acid, weight gain was suppressed, blood glucose and plasma triglycerides were controlled to low values, and rapid rises in blood glucose following the ingestion of food were suppressed. Moreover, in streptozotocin-induced diabetes rats elevation of blood glucose was suppressed with itaconic acid. Thus, itaconic acid was confirmed to have not only an obesity preventing effect, but also an antidiabetic effect and an antilipemic effect. Based on these findings, the inventors accomplished the present invention. Itaconic acid was notified as being included in the List of Food Additives in 1996 by the Director-General, Environmental Health Bureau, Ministry of Health and Welfare, Japan, but its use was restricted to an acidulant.

EMBODIMENTS OF THE INVENTION

The present invention will now be described in more detail. To solve the aforementioned problems, the inventors conducted extensive studies. As a result, they speculated that if glycolytic pathway metabolism in the liver can be suppressed following food ingestion, lipid synthesis could be suppressed, and rapid rises in blood glucose following the ingestion of food could also be suppressed, whereby prevention or an improvement in obesity, hyperlipidemia and diabetes could be expected. Based on this speculation, they focused on fructose 2,6-bisphosphate (F26BP) which is a regulatory factor for phosphofructokinase (PFK), a regulatory enzyme for glycolytic pathway metabolism, and fructose-6-phosphate-2-kinase:fructose 2,6-bisphosphatase bifunctional enzyme (F6P2kinase:F26Pase) which forms the F26BP. The enzyme activity of this bifunctional enzyme is affected by Glycerol 3-P, PEP, 3-P-glycerate, and 2-P-glycerate which are metabolites of the glycolytic pathway. The finding that these wide-ranging compounds showed a similar enzyme regulating action suggested that the specificity of the F6P2kinase:F26Pase protein for these regulatory factors was not severly limited.

The inventors made in-depth studies of compounds similar in structure to PEP, one of the regulatory factors for the bifunctional enzyme, and identified inhibitory activity against F6P2kinase exerted by itaconic acid. They also mixed itaconic acid with drinking water, and gave the mixture to rats orally, confirming curtailment of weight gain, a significant decrease in body fat, significant decreases in blood glucose and plasma triglycerides, and suppression of rapid rises in blood glucose following the ingestion of food. They also confirmed that a rise in blood glucose was suppressed by ingestion of itaconic acid even in rats with streptozotocin-induced hyperglycemia.

Elucidation of the mechanism of regulation of glycolytic pathway metabolism may lead to the discovery of substances, other than itaconic acid, which are active in inhibiting F6P Kinase and which are highly safe. Such substances can be used for the purpose of the present invention.

Itaconic acid used in the invention is produced by industrially culturing a koji mould (*Aspergillus terreus*, *A. itaconicus*) in a sugar cane medium (Seikagaku Jiten (Dictionary of Biochemistry), 2nd Edition, Tokyo Kagaku Dojin Publishing Company). According to "Seibutsugaku Jiten" (Dictionary of Biology; 3rd Edition, Iwanami Shoten Publishing Company), itaconic acid is produced in large amount by the culture of a mould, especially, *Aspergillus itaconicus* growing on the surface of ume (Japanese apricot) vinegar. As sugar sources in the culture, beet as well as sugar cane is used. Other sugar sources may be used to produce itaconic acid. The production of microorganisms is not restricted to the above two types, and any microorganisms which produce itaconic acid can be used for the purpose of the invention.

In addition to microbial production, itaconic acid can be produced by distilling aconitic acid to form itaconic anhydride and citraconic anhydride, and heating the former compound together with water ("Rikagaku Jiten" (Dictionary of Physics and Chemistry; 3rd Edition, Iwanami Shoten Publishing Company). Therefore, itaconic acid can also be synthesized chemically, and itaconic acid, whether microbiologically produced or chemically synthesized, may be used in the invention.

Itaconic acid can be used unchanged in acid form, or may be used as a salt. Examples of the salt are sodium salt and potassium salt, but other salts may also be used. Itaconic acid can be added to foods, since it is listed for as a use as an acidulant in "the Notifications of Laws and Ordinances Related to Lists of Existing Additives Associated with Revision of the Food Sanitation Law (Edited by Food Chemistry Division, Environmental Health Bureau, Ministry of Health and Welfare, Japan, published by Japan Food Additives Association, May 1996)".

However, itaconic acid is strongly acidulous, and thus is difficult to consume in the form of a beverage or food in an amount sufficient to exert an antiobesity, antidiabetic and/or antilipemic effect. In attempting to overcome this problem, studies by the inventors revealed that neutralization of itaconic acid for conversion to an itaconic acid salt eliminates its acidulous taste and facilitates its ingestion as a food or beverage. Any salt of itaconic acid can be employed, with the proviso that they can be added to foods. Examples include alkali metal salts such as sodium salt and potassium salt; alkali earth metal salts such as calcium salt and magnesium salt; and basic amino acid salts.

Itaconic acid or its salt, used as a glycolytic pathway metabolic regulator in the invention, can be provided in various forms, including foods such as functional foods, or drugs. Edible and drinkable forms in the invention include any forms of edible compositions composed of the above-described itaconic salts as active ingredients, and carriers acceptable as edible or drinkable foodstuffs. For example, itaconic acid or its salt can be formed into any type of edible or drinkable form, including solid foods such as bread, chewing gum, cookies, chocolate, confectionery, and cereals,; jammy or gel-like foods such as jam, ice cream, yogurt, and jelly; and beverages such as juice, coffee and cocoa. Alternatively, itaconic acid or its salt can be incorporated into seasonings, spices, and other food additives.

The daily intake of itaconic acid is not restricted, in so far as it exhibits the desired effect of the invention. Daily intake is preferably 0.1 to 100 g, and more preferably 1 to 10 g.

Obesity as used herein does not refer simply to a state where body weight is excessive, but rather to a state in which the proportion of adipose tissues in the constituents of the body has increased abnormally. In recent years, reports on the accumulation of subcutaneous fat and visceral fat have been issued showing that visceral fat type obesity involving fat accumulated among organs tends to contribute to adult diseases such as hypertension, hyperlipidemia, and diabetes, in comparison with subcutaneous fat type obesity involving fat accumulated in subcutaneous tissue. Since itaconic acid also suppresses a buildup of visceral fat, it can be expected to have a preventative effect against these diseases as well as against obesity.

Acarbose (Bayer Yakuhin) and voglibose (AO-128, Takeda Chemical Industries), which are carbohydrate degradation enzyme inhibitors currently used as drugs, have been confirmed in animal studies and clinical trials to have the effect of suppressing rapid increases (peaks) in postprandial blood glucose. The efficacy of these drugs against diabetes as well as obesity has also been reported (Res. Exp. Med. Vol. 175, page 87, 1979, H. Odaka and T. Matsuo, Journal of the Agricultural Chemical Society of Japan, Vol. 63, 217–219, 1989, M. Ikeda, H. Odaka and T. Matsuo, Basic Pharmacology & Therapeutics, Vol. 19, No. 10, 4105–4117, 1991). Likewise, itaconic acid suppressed rapid increases (peaks) in postprandial blood glucose, and its ingestion for 3 weeks was confirmed to have a tendency toward decreasing blood glucose and plasma triglycerides. Thus, itaconic acid is considered to be optimal, particularly in alleviating non-insulin dependent diabetes mellitus accompanied by obesity. This compound was also confirmed to be effective in a streptozotocin-induced diabetes model regarded as an insulin-dependent diabetes model. Hence, the compound is considered to be effective in improving not only non-insulin-dependent diabetes mellitus, but also insulin-dependent diabetes mellitus.

The present invention uses foods, drinks or drugs containing itaconic acid or its salt as an active ingredient, and can provide safe foods, drinks and drugs, which are substantially free from adverse reactions while exerting an effect in decreasing body fat.

The present invention will now be described in greater detail by way of Examples, which are not limitative of the invention.

EXAMPLE 1

Figure 1:
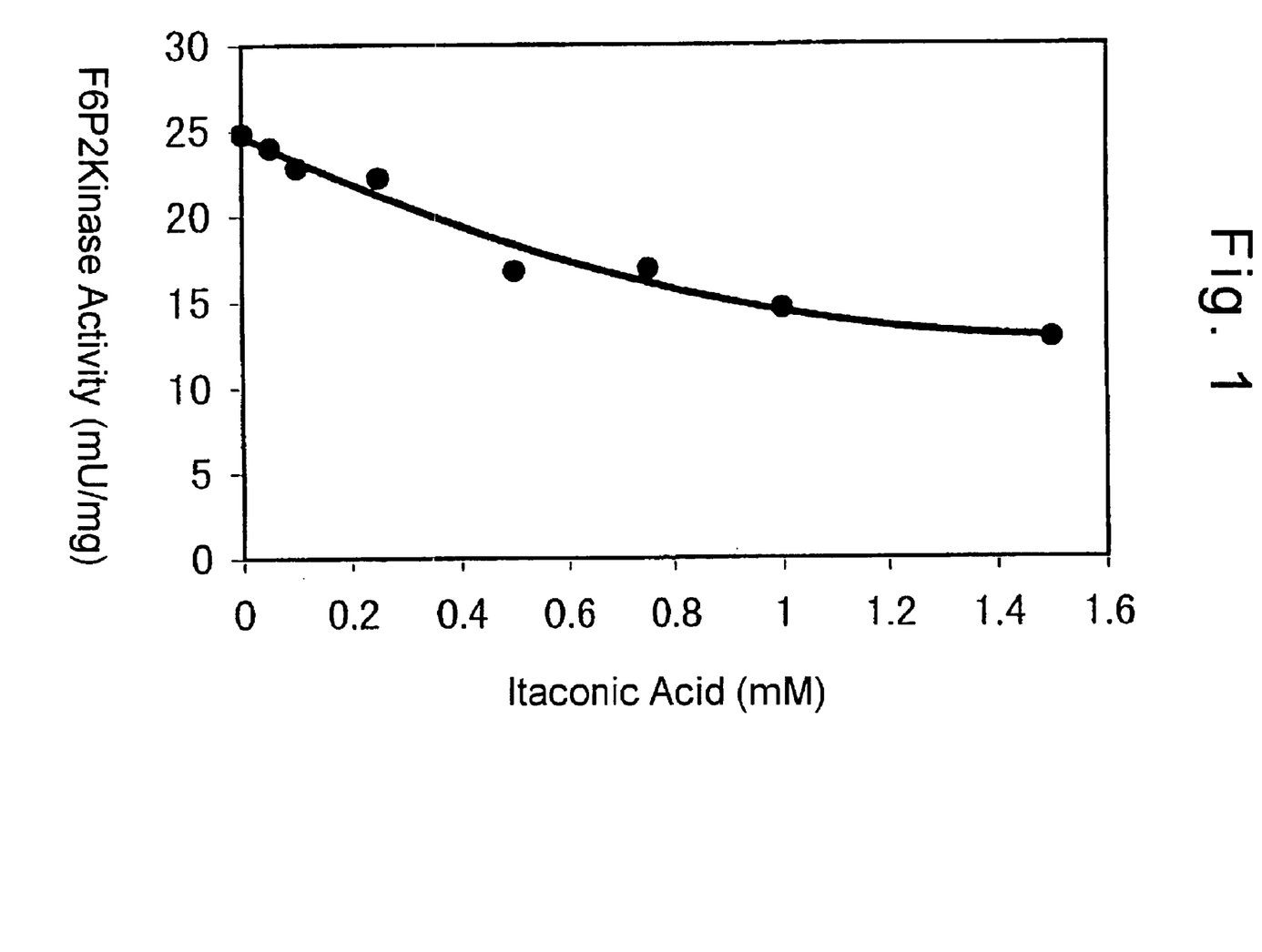
FIG. 1 is a graph showing the results of a test described in Example 1, indicating the inhibitory effect of itaconic acid on the activity of F6P2kinase which catalyzes a reaction for synthesis of F26BP.

Inhibition by Itaconic Acid of F6P2kinase Activity Catalyzing Synthetic Reaction for F26BP The gene for rat liver type F6P2kinase was incorporated into *Escherichia coli* and expressed. From the *E. coli* cells, rat liver type F6P2kinase was purified (K. Kitamura et al., J. Biol. Chem., Vol. 264, 9799–9806, 1989). The rat liver type F6P2kinase (1.25 µg) was reacted at 30° C. in a reaction solution containing 100 mM Tris-HCl (pH 7.5), 0.1 mM EDTA, 10 mM $MgCl_2$, 2 mM ATP, 0.4 mM F6P, and 0 to 1.5 mM itaconic acid. After lapses of 2, 4 and 6 minutes, 10 µl of the reaction mixture was transferred into a test tube containing 90 µl of 50 mM NaOH, and heated for 1 minute at 90° C. to terminate the reaction. The amount of the resulting F26BP was measured by a change in absorbance due to oxidation of NADH upon subsequent addition of glycolytic pathway enzymes. That is, 10 µl of the reaction mixture after termination of the reaction was added to 1 ml of a reaction solution containing 50 mM HEPES (pH 7.3), 0.2 mM EDTA, 5 mM $MgCl_2$, 1 mM F6P, 1 mM PPi, 15 mU PPi-F6P phosphotransferase, 0.15 mM NADH, 1 U aldolase, 1 U glycerol-3-phosphate dehydrogenase, and 10 U triose-phosphate isomerase. The amount of F26BP was measured by a decrease in the absorbance at 340 nm (Van Schaftingen et al., Eur. J. Biochem., Vol. 129, 191–195, 1982). The activity that converts the substrate F6P to 1 µmole F26BP over 1 minute at 30° C. is defined as 1 U. The results are shown in FIG. 1. An inhibitory activity of about 30% was observed with 0.5 mM itaconic acid.

EXAMPLE 2

Evaluation of Preventive Effect on Obesity in Rats

Male SD rats (8-week-old) were individually reared, commencing immediately after arrival. After a week of acclimatization, the animals were divided into a control group and an itaconic acid group (8 animals per group), and reared for 3 weeks, with feed and drinking water of the itaconic acid concentration shown in [Table 1] being given ad lib.

TABLE 1

| | Itaconic acid concentration in drinking water (mg/ml) | | | |
|---|---|---|---|---|
| Day of experiment | Day 1 | Days 2–3 | Days 4–5 | Days 6–22 |
| Control group | 0 | 0 | 0 | 0 |
| Itaconic acid group | 2.5 | 5 | 7.5 | 10 |

During the 3-week rearing period, the body weight, the feed intake, and the water intake were measured daily or every other day. On the final day, the animal was placed on a 17-hour fast, the blood was sampled, and the plasma was analyzed for blood glucose, hepatic function, and lipid-related parameters. Furthermore, the weight of the livers, kidneys, fat around the kidneys, and fat around the intestines was measured. The experiments were conducted in groups of 8 rats each, and the results were indicated as mean values±standard deviations. The test for a significant difference was performed by the analysis of variance of data, followed by Student t-test. The level of significance was set at 0.05.

Figure 2:
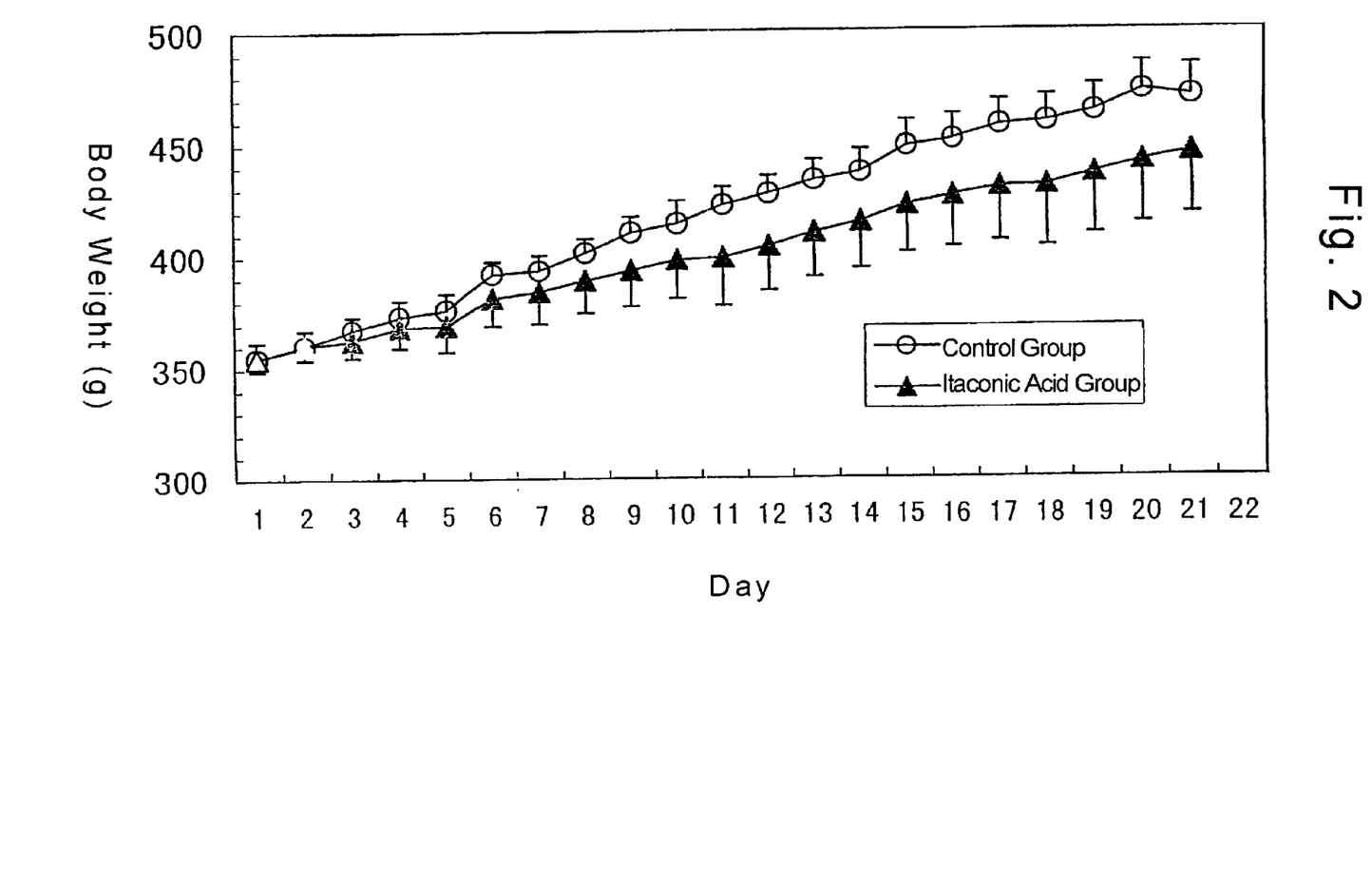
FIG. 2 is a graph showing the results of a test described in Example 2, indicating the suppressive effect of itaconic acid ingestion on weight gain.
Figure 3:
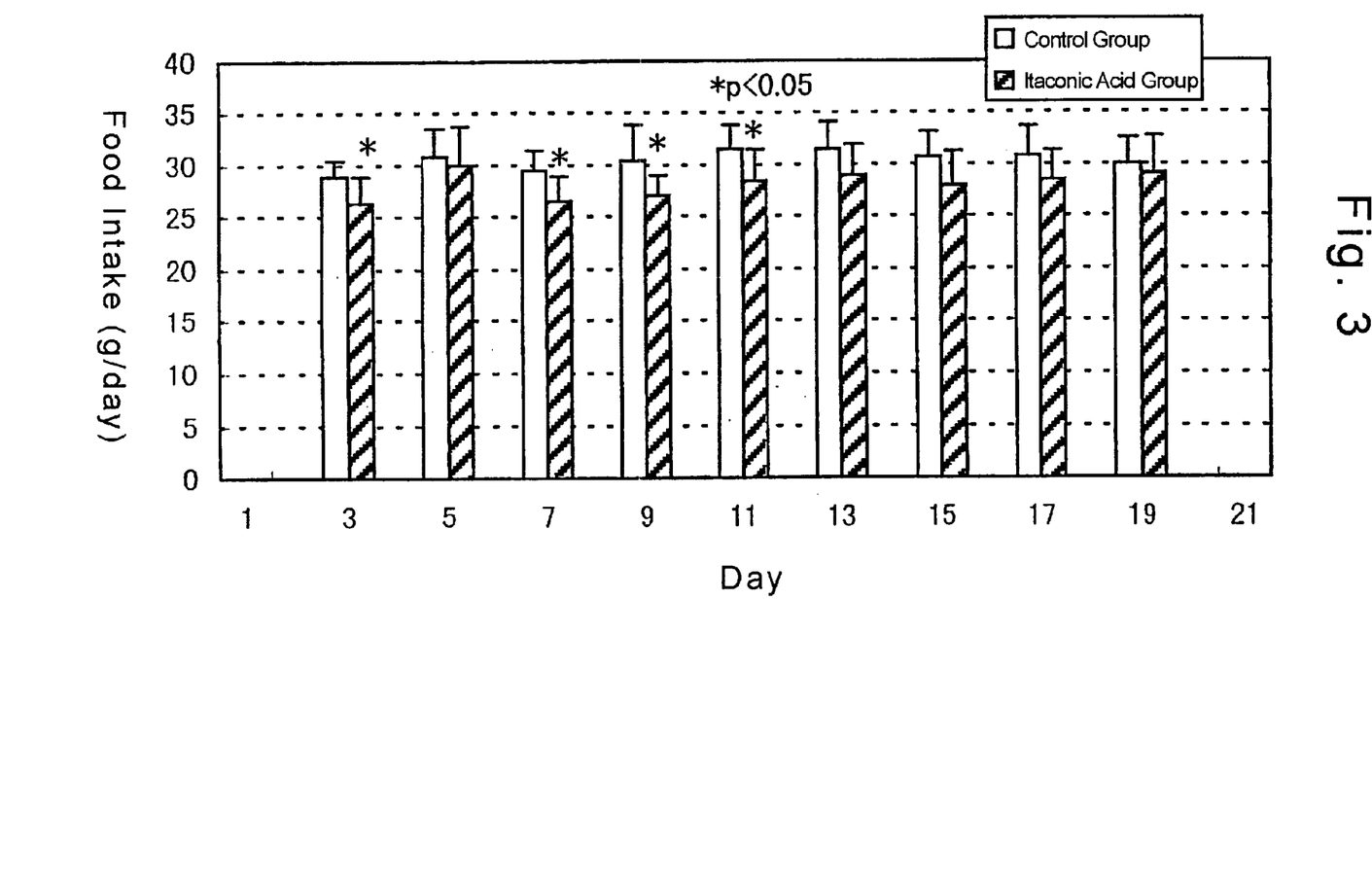
FIG. 3 is a graph showing changes in feed intake during the test period of Example 2.
Figure 4:
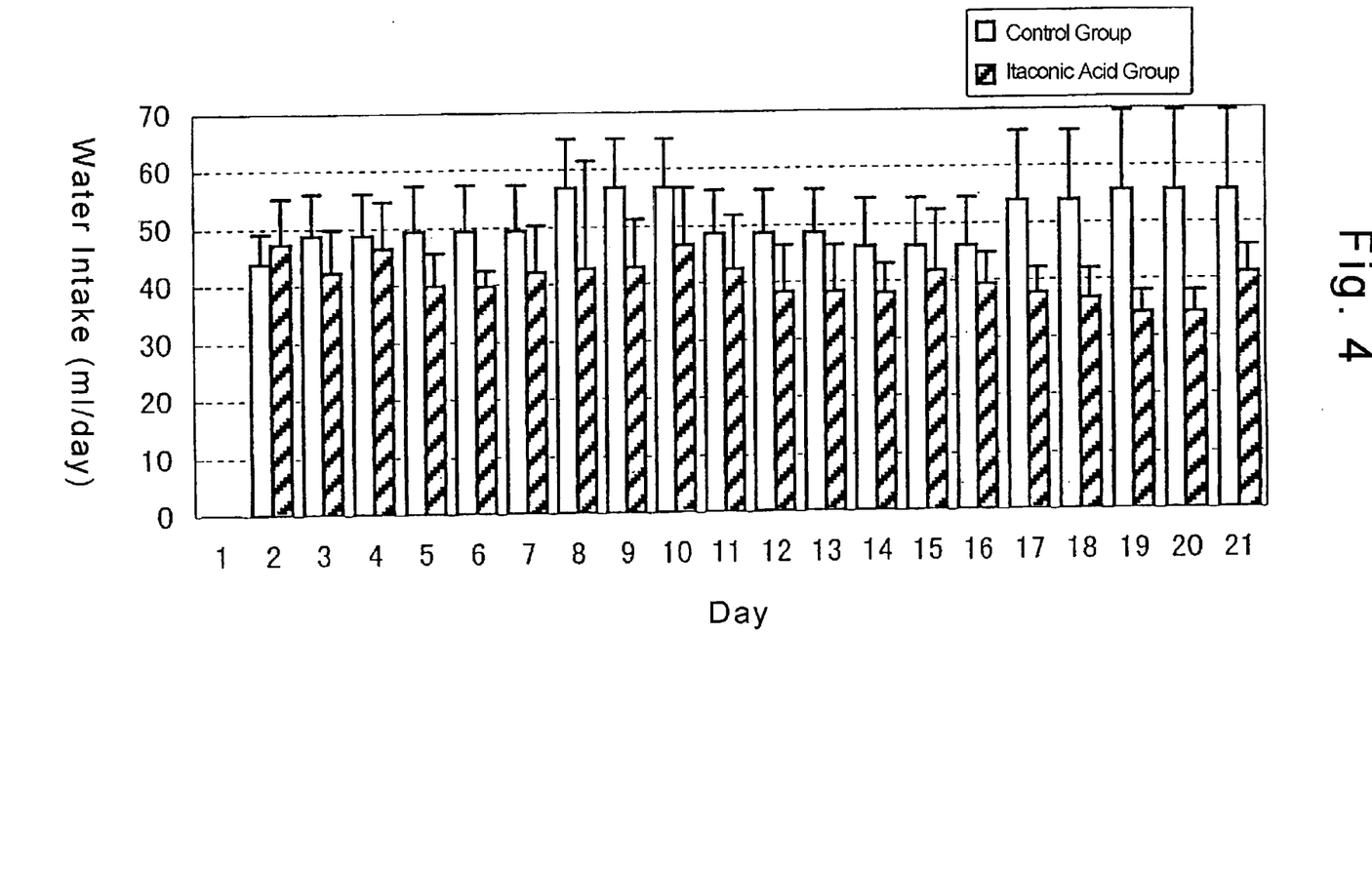
FIG. 4 is a graph showing changes in water intake during the test period of Example 2.

As shown in [FIG. 2], significant suppression of weight gain was observed in the itaconic acid group from Day 9 onwards (p<0.05 against the control group). In the itaconic acid group, decreases in the feed intake were observed compared with the control group, as shown in [FIG. 3]. The water intake showed a similar tendency, as shown in [FIG. 4]. The dose of itaconic acid administered was calculated from the following equation using the body weight and the water intake per animal per day:

Dose of itaconic acid per body weight=Daily water intake×Itaconic acid concentration/body weight The dose of itaconic acid was an average of 871±207 mg/kg/day throughout the experiment period, or an average of 943±123 mg/kg/day during the period in which 10 mg/ml was administered.

The plasma collected at completion of the experiments was measured for various biological parameters. As shown in Table 2, the blood glucose, triglycerides, and free fatty acids decreased significantly, but the other parameters showed no clear differences from the control group. The experiments were conducted in groups of 8 rats each, and the results were indicated as mean values±standard deviations. The test for a significant difference was performed by the analysis of variance of data, followed by Student t-test. The level of significance was set at 0.05.

TABLE 2

|  | GOT (IU/l) | GPT (IU/l) | ALP (IU/l) | LDH (IU/l) |
|---|---|---|---|---|
| Control group | 65.0 ± 7.2 | 14.4 ± 2.1 | 0.3 ± 0.2 | 275 ± 56 |
| Itaconic acid group | 65.0 ± 12.0 | 13.0 ± 2.5 | 0.3 ± 0.1 | 276 ± 82 |

|  | Total bilirubin (mg/dl) | Total cholesterol (mg/dl) | Free cholesterol (mg/dl) |
|---|---|---|---|
| Control group | 0.18 ± 0.02 | 47.7 ± 5.4 | 11.9 ± 1.8 |
| Itaconic acid group | 0.19 ± 0.02 | 46.3 ± 7.1 | 12.2 ± 2.0 |

|  | Triglycerides (mg/dl) | Blood glucose (mg/dl) | Free fatty acids (mg/dl) |
|---|---|---|---|
| Control group | 42.8 ± 13.3 | 169 ± 18 | 292 ± 67 |
| Itaconic acid group | 20.9 ± 2.8** | 149 ± 19* | 199 ± 75* |

*P < 0.05; **P < 0.01

Figure 5:
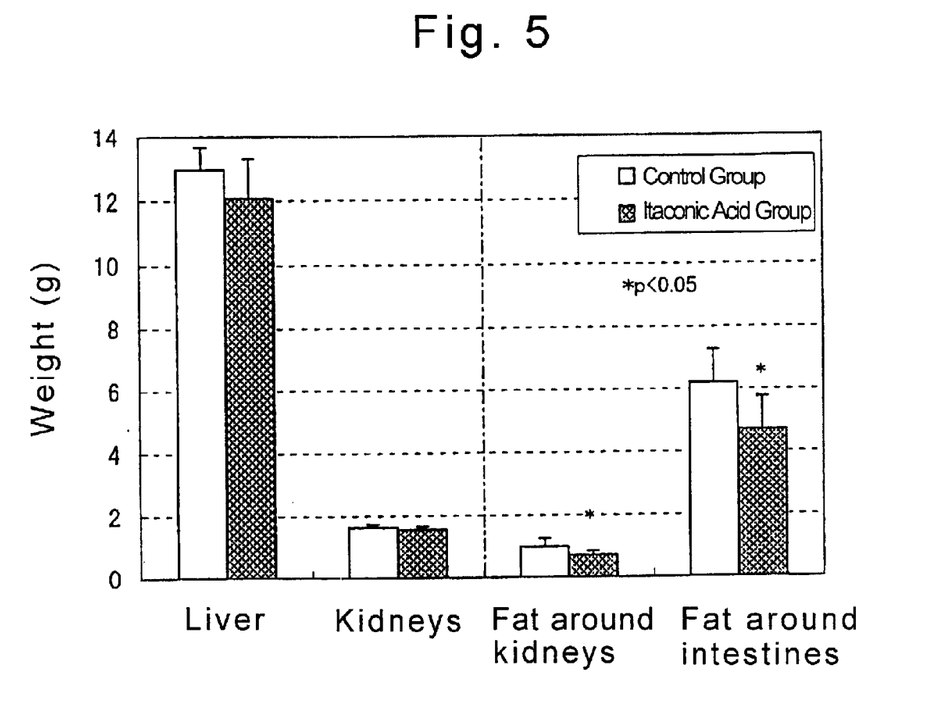
FIG. 5 is a graph showing the weights of the livers and kidneys, and fats around the kidneys and intestines, per 100 g of body weight at completion of the test period of Example 2.

As shown in [FIG. 5], the weights of the organs per 100 g of the body weight was not different between the groups for the livers and the kidneys. However, the weights of fat per 100 g of the body weight were significantly decreased in the itaconic acid group for both of the fat around the kidneys and the fat around the intestines ($p<0.05$).

Based on the above findings, a body weight gain suppressing effect and a fat weight decreasing effect were obtained in the group receiving itaconic acid from drinking water for 3 weeks. Thus, itaconic acid was demonstrated to prevent obesity. Since itaconic acid shows an inhibitory effect on F6P2kinase, it may have decreased the formation of F26BP thereby suppressing the activity of PFK. Furthermore, itaconic acid is assumed to have suppressed the metabolic activity of the glycolytic pathway to hold back the synthesis of acetyl-CoA, thereby curtailing lipid synthesis. There is also the possibility that glucose, which was not metabolized in the glycolytic pathway because of the above mechanism, was utilized for glycogen synthesis. Thus, the decrease in postprandial blood glucose may have been curbed, with the result that food intake may have decreased. Both of these mechanisms may have worked additively or synergistically, leading to a body weight gain curbing action and a fat weight decreasing action.

The results of analysis of the biochemical parameters in the plasma showed a tendency toward significant decreases in blood glucose and triglycerides in the itaconic acid group. Thus, efficacy against diabetes and hyperlipidemia (especially, non-insulin-dependent diabetes mellitus) can be expected. In terms of other parameters, there was no intergroup difference. Thus, the safety of itaconic acid was shown to be high.

EXAMPLE 3

Evaluation of the Suppressive Effect on Blood Glucose Elevation in Rats

Male SD rats (weighing 300 to 400 g), operated on for blood sampling cannulation into the femoral artery, were used. After an overnight fast, itaconic acid (500 mg/kg) was orally administered. Thirty minutes later, glucose (4 g/kg) was ingested, and changes in blood glucose were observed. In the control group, purified water, free of itaconic acid, was orally administered in the same volume. Experiments were conducted in groups of 4 rats each, and the results were indicated as mean values±standard deviations. The test for a significant difference was performed by the analysis of variance of data, followed by Student t-test. Differences were taken as significant when p values were less than 0.05 (*p<0.05, **p<0.01).

Figure 6:
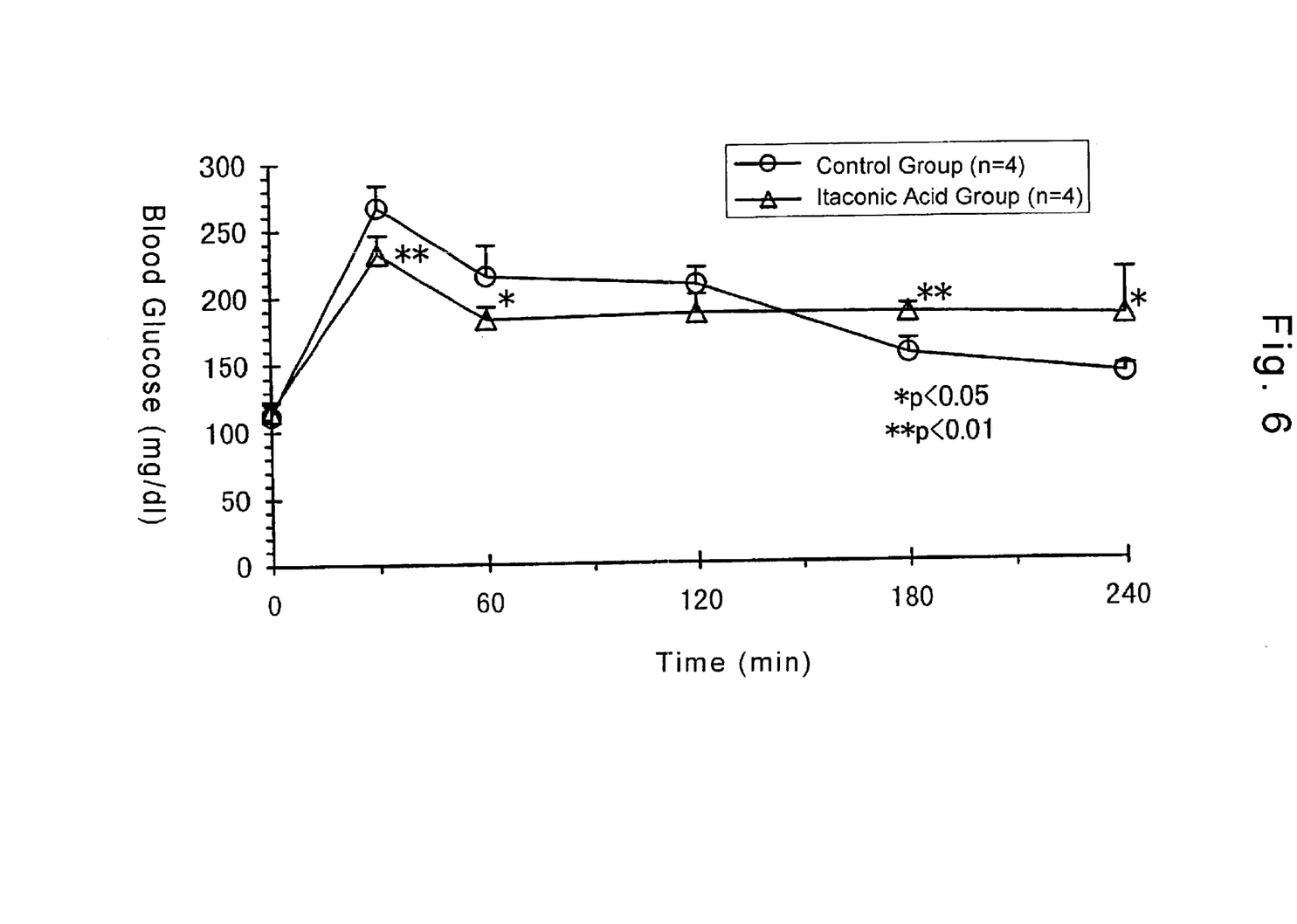
FIG. 6 is a graph showing the results of a test described in Example 3, indicating effect of preingested itaconic acid changes in blood glucose after ingestion of glucose.

As shown in FIG. 6, blood glucose rapidly rose in the control group 30 minutes after the glucose challenge, and then lowered, returning to nearly pre-challenge values in 120 minutes. In the itaconic acid group, an initial rapid increase in blood glucose was significantly curbed, and blood glucose was then observed to lower slowly. The blood glucose increase curbing effect during the initial peak may have been attributed to accelerated glycogen synthesis due to the suppressive effect of itaconic acid on metabolism of the glycolytic pathway. During the subsequent lowering of blood glucose, on the other hand, gluconeogenesis from glycogen may have occurred, resulting in a slow fall in blood glucose.

The excessive secretion of insulin triggered by a rapid rise in blood glucose after glucose challenge accelerates the uptake of glucose into fat cells to promote lipid synthesis. It also imposes a burden on the liver and pancreas. After many years, these states may develop into non-insulin-dependent diabetes mellitus (W. Puls, U. Keup, H. P. Krause, L. Muller, D. D. Schmidt, G. Thomas, E. Tsuscheit, Front. Horm Res. Vol. 7, 235–247, 1980). The slow increase and the slow decrease in blood glucose noted in the itaconic acid pretreatment group of the experiments are judged to lead to the prevention of diabetes, obesity and hyperlipidemia in healthy persons as well as patients with non-insulin-dependent diabetes mellitus.

In the experiments, blood glucose was significantly high in the itaconic acid group even after 180 minutes and 240 minutes when blood glucose had already lowered in the control group. It is common knowledge that a fall in blood glucose creates a feeling of hunger. The small feed intake in the itaconic acid group in the 3-week ingestion experiments shown in Example 2 may reflect a decreased feeling of hunger.

EXAMPLE 4

Evaluation of Suppressive Effect on Blood Glucose Elevation in Streptozotocin-induced Diabetes Rats Streptozotocin is an antibiotic derived from Streptomyces achromogenes, one of filamentous fungi. Its action of inducing insulin-dependent diabetes mellitus was reported for the first time in 1963 by Rakieten et al. (Rakieten N, Rakieten M L, Nadkarni M V, Cancer Chemother Rep 29:91–98, 1963). Since then, it has been used most commonly as a substance for inducing diabetes experimentally. The main mechanism of its diabetogenic action is ascribed to the destruction of P cells of the pancreas, thereby suppressing insulin secretion. In male Wistar rats (7-week-old), a solution of streptozotocin in 0.05 M citric acid-0.145 mM NaCl (pH 4.5) was administered into the caudal vein (50 mg/kg). The animals were individually reared, commencing immediately after administration of streptozotocin. After a lapse of 48 hours, the animals with blood glucose levels of 300 mg/dl or more were divided into a control group and an itaconic acid group (7 or 8 animals per group), and study was initiated. A rearing feed was given to the control group, and a rearing feed containing 1.38% of itaconic acid was given to the itaconic acid group, ad. lib. together with drinking water, and the animals were reared for 3 weeks.

During the 3-week rearing period, blood glucose, body weight, feed intake, and water intake were measured twice or 3 times weekly. Rats are nocturnal animals, and feeding mostly takes place at night. However, since their blood glucose fluctuates greatly depending on the elapsed time after eating, each measurement of blood glucose was made between 9:30 and 10:00 in the morning. Blood hemoglobin A1c was measured on the day after administration of streptozotocin and on the 19th day after start of the study. Hemoglobin A1c is hemoglobin having glucose attached thereto non-enzymatically, and is expressed as a percentage (%) of total hemoglobin. In humans, hemoglobin A1c is known to serve as an indicator of the mean value of blood glucose during the period from 1 to 3 months previously until blood sampling. In rats, the life of an erythrocyte is about half of that in humans, and hemoglobin A1c has been reported to reflect the mean value of blood glucose since 2 to 3 weeks previously.

The experiments were conducted in groups of 7 or 8 rats each, and the results were indicated as mean values±standard deviations. The blood glucose was expressed as changes in individual animals compared with the value found at the start of the study (grouping). The test for a significant difference was performed by the analysis of variance of data, followed by Student t-test. The level of significance was set at 0.05.

Figure 7:
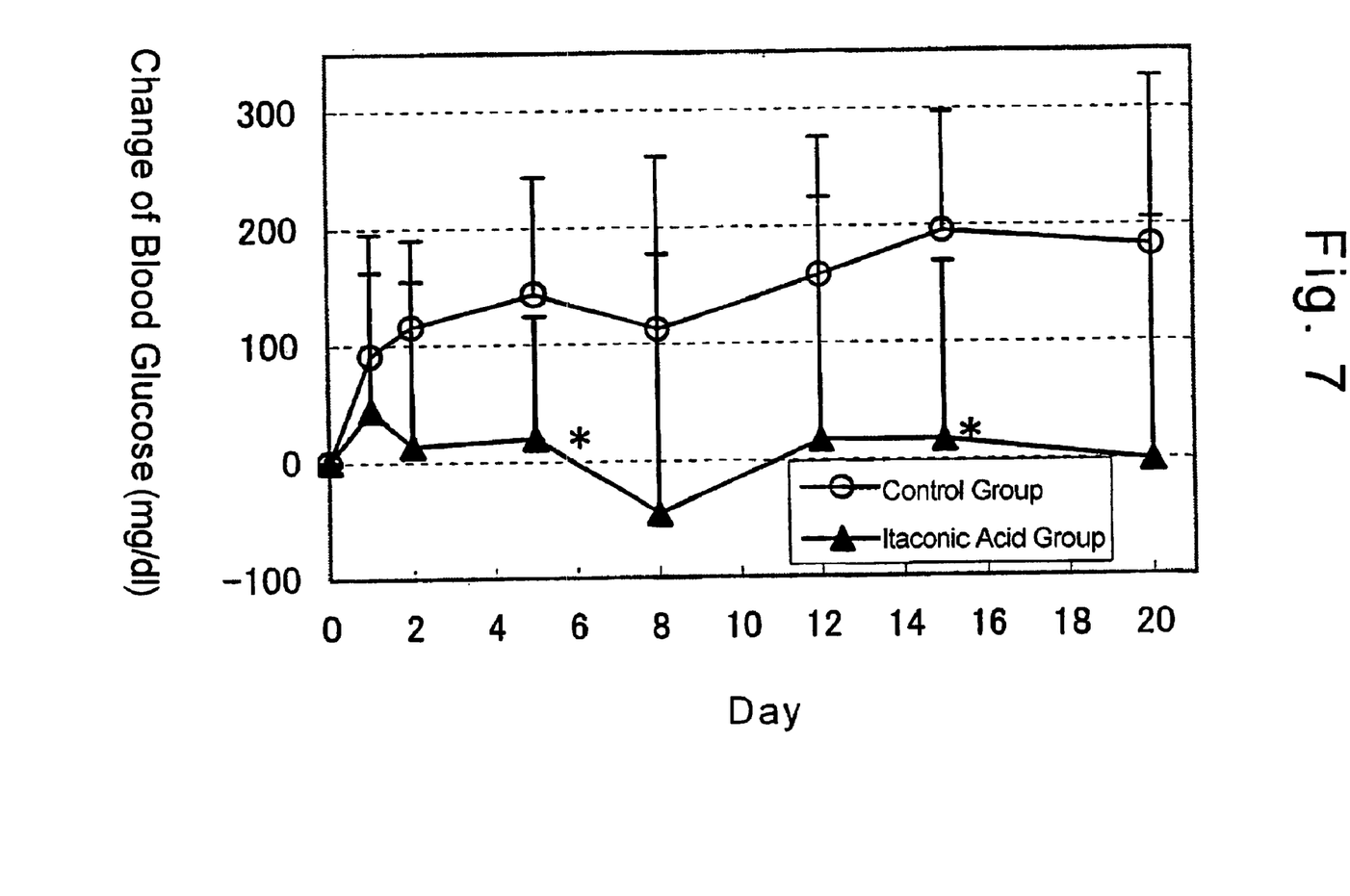
FIG. 7 is a graph showing the results of a test described in Example 4, indicating the suppressive effect of itaconic acid ingestion on elevation of blood glucose.
Figure 8:
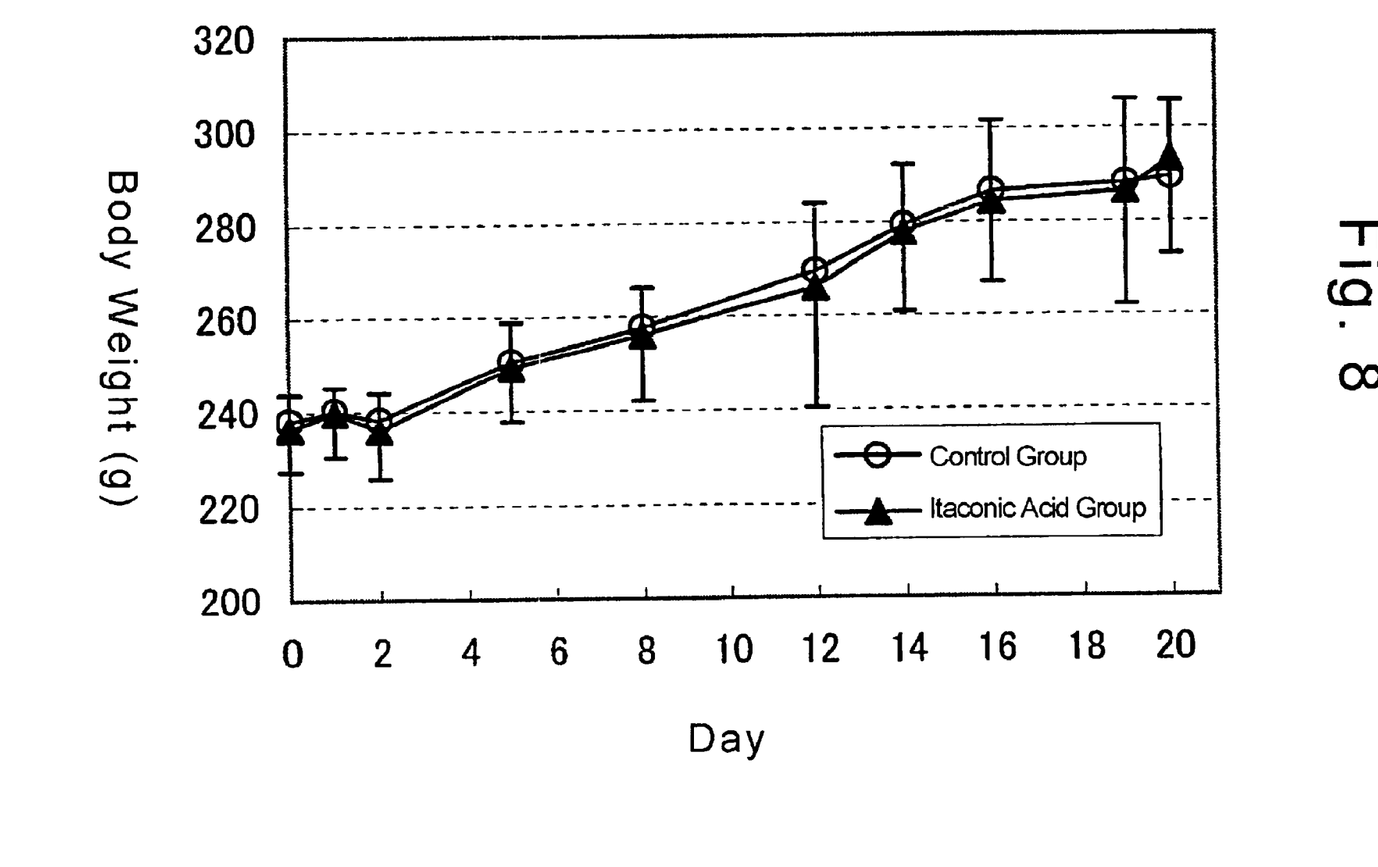
FIG. 8 is a graph showing changes in body weight during the test period of Example 4.
Figure 9:
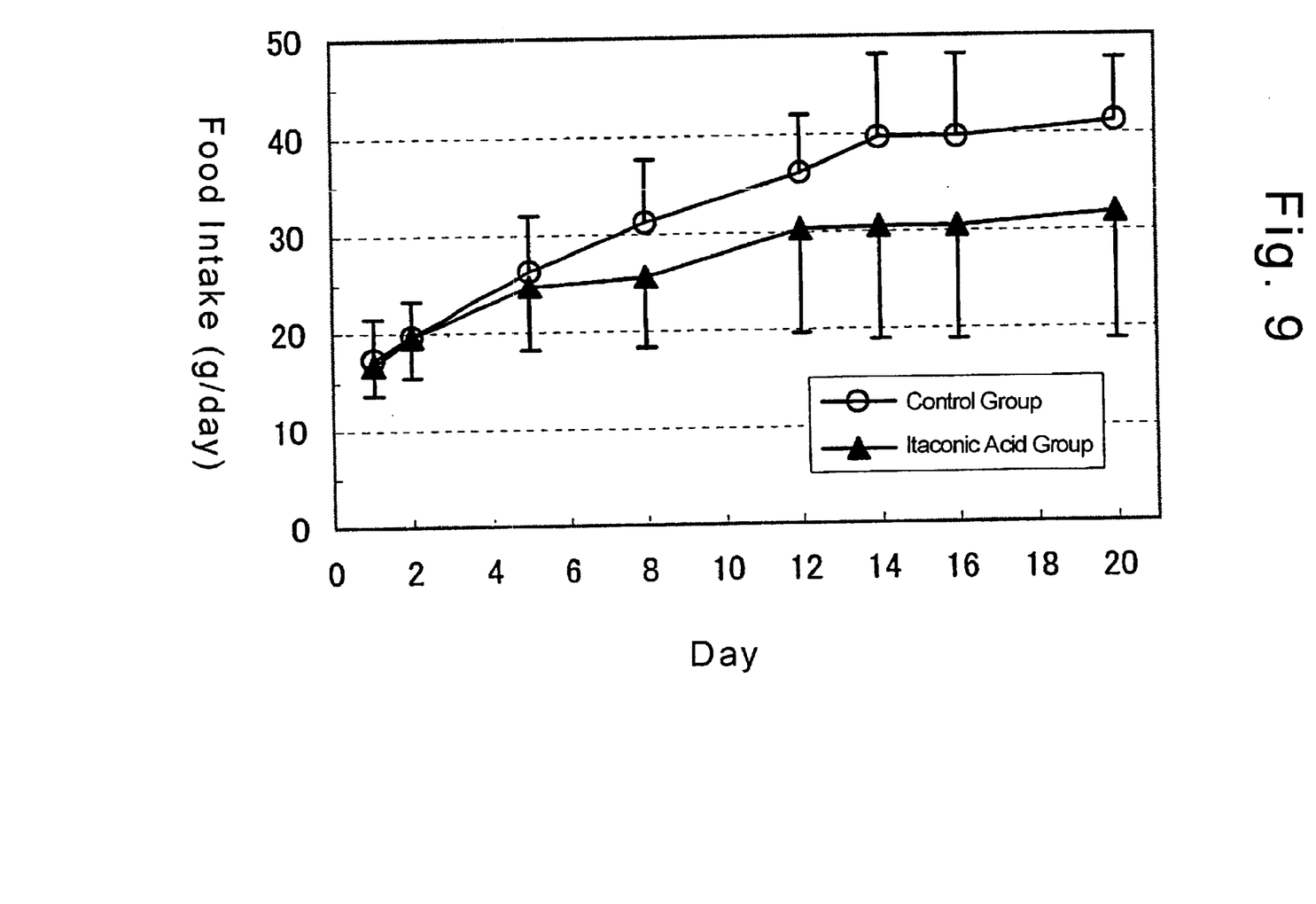
FIG. 9 is a graph showing changes in feed intake during the test period of Example 4.
Figure 10:
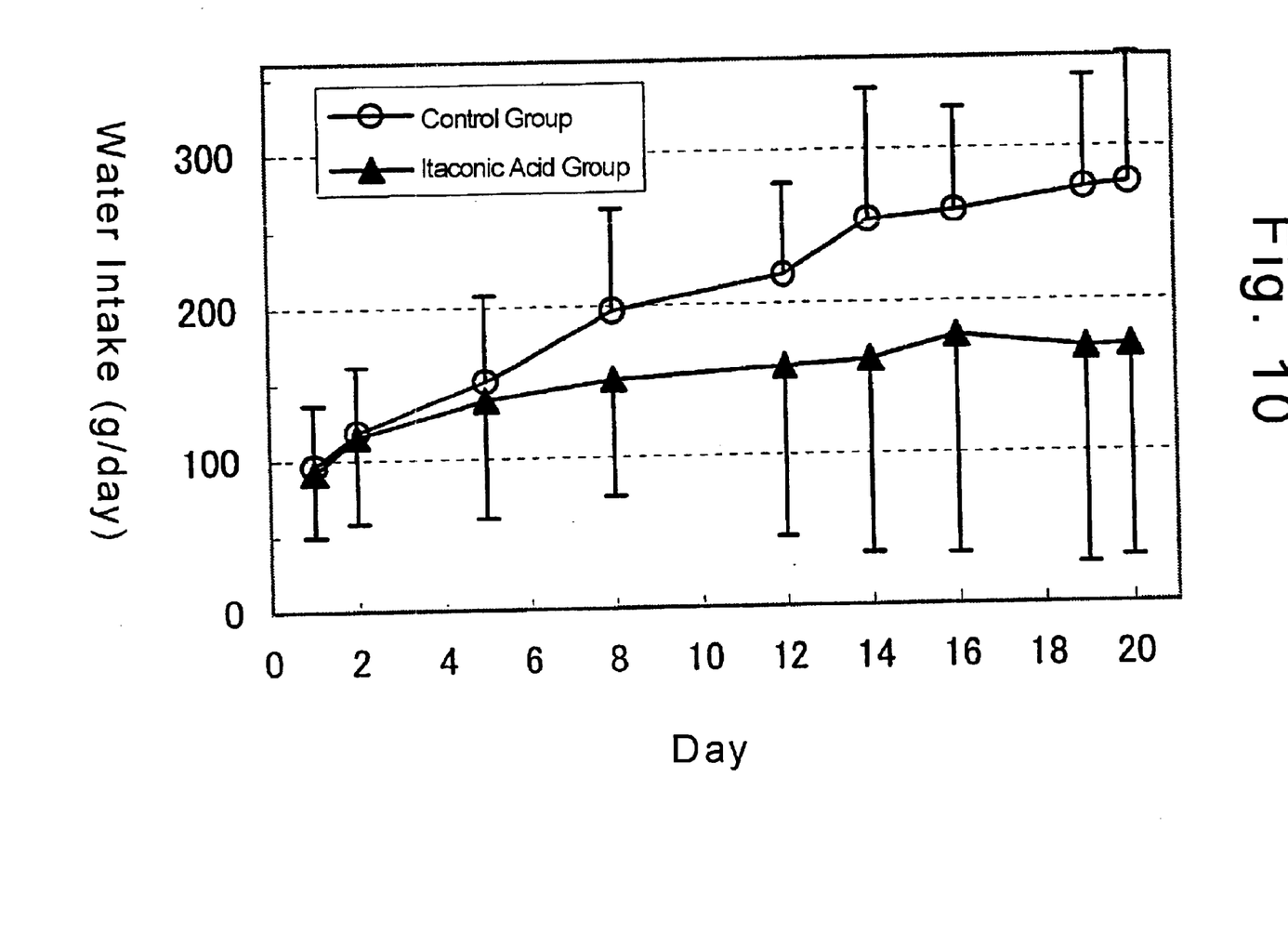
FIG. 10 is a graph showing changes in water intake during the test period of Example 4.

As shown in FIG. 7, suppression of the rise in blood glucose was observed in the itaconic acid group from Day 1 onwards, and significant differences existed between the groups (p<0.05 against the control group) on Days 5 and 15. The body weight was not different between the groups, as shown in FIG. 8. In the itaconic acid group, decreases in feed intake were observed, from about Day 5 onwards, compared with the control group, as shown in FIG. 9. The water intake showed a similar tendency, beginning at the same time point, as shown in FIG. 10. Feed intake and water intake are known to generally increase in experimental animals as diabetes progresses. In the present study, the suppressive effect on the elevation of blood glucose was noted after initiation of the study, and then the actions of curbing increases in feed intake and water intake occurred, in the itaconic acid group. These findings suggest that the curtailment of increases in feed intake and water intake by administration of itaconic acid may have resulted from the suppression of the progression of diabetes.

Figure 11:
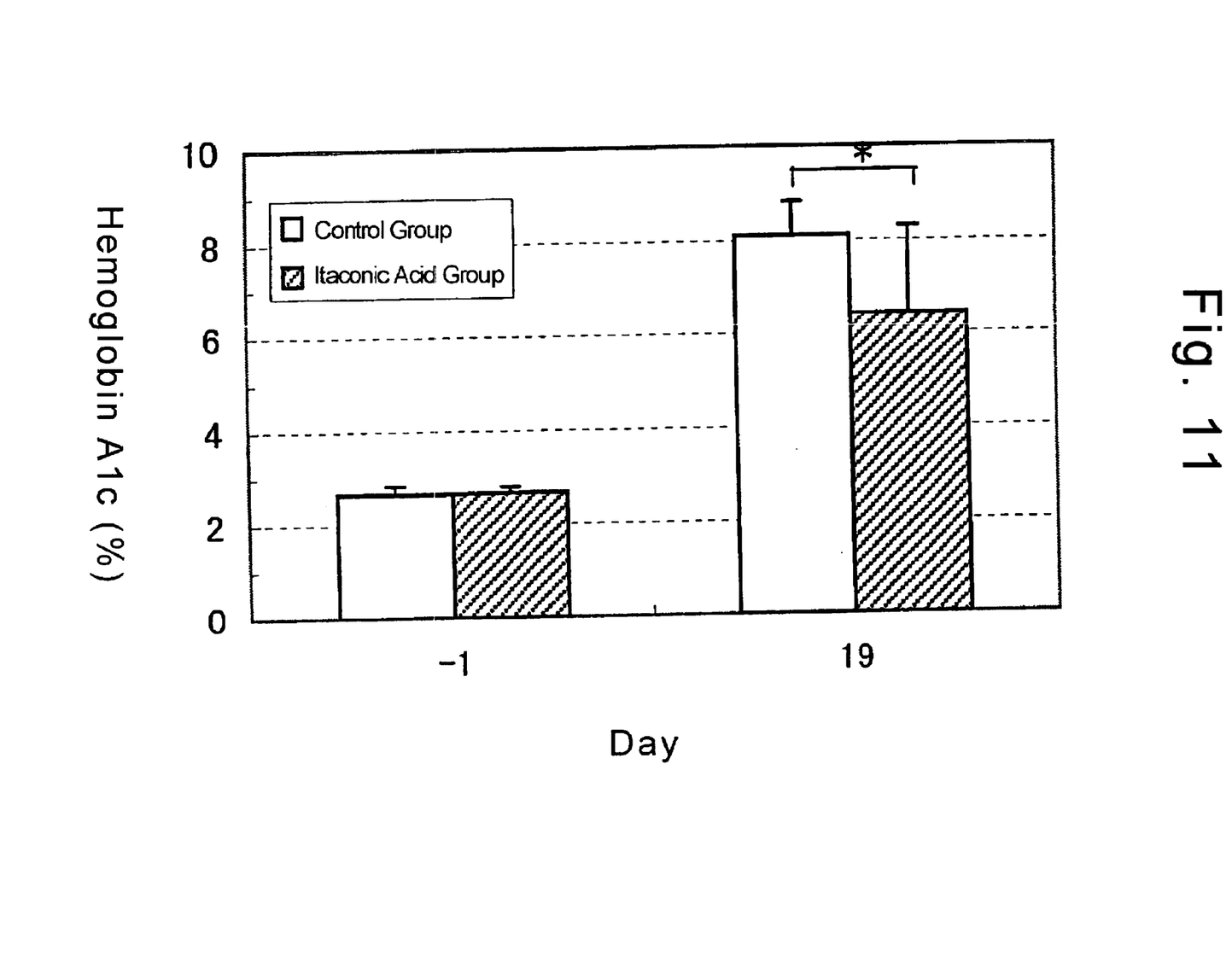
FIG. 11 is a graph showing blood hemoglobin Alc at start and completion of the test of Example 4.

Furthermore, as shown in FIG. 11, blood hemoglobin A1c increased in both groups on Day 19, but a significant curbing of the rise in blood hemoglobin A1c was noted in the itaconic acid group compared with the control group. The dose of itaconic acid administered was calculated from the following equation using the body weight and food intake per animal per day:

$$\text{Dose of itaconic acid per body weigh} = \text{Daily feed intake} \times \text{Itaconic acid concentration/body weight}$$

The dose of itaconic acid was found to be an average of 1,412±526 mg/kg/day throughout the study period.

The above results demonstrated that the effect of suppressing a rise in blood glucose caused by streptozotocin treatment was obtained in the group receiving itaconic acid from feed.

INDUSTRIAL APPLICABILITY

A decrease in body fat, and prevention of obesity can be achieved by taking a drug or a food or beverage which contains an effective amount of itaconic acid produced by the present invention. Moreover, diseases associated with obesity such as diabetes, hypertension, and hyperlipidemia, can be prevented or improved by the use of such a drug, food or beverage. Furthermore, a dieting effect can be obtained when the drug, food or beverage is combined with an ordinary food or drink. The drug, food and beverage of the invention, even when taken for a long term, substantially cause no adverse reactions, and are safe.

What is claimed is:

1. A method of inhibiting the enzyme, fructose-6-3 phosphate-2-kinase, by administering to a person in need of such enzyme inhibition, an enzyme inhibiting effective amount of itaconic acid or a salt thereof as active component of a food or beverage.

2. A pharmaceutical composition, which is a drug for alleviating obesity, comprising itaconic acid or a salt thereof as a fructose-6-phosphate-2-kinase inhibitor, and a pharmaceutically acceptable carrier.

3. A pharmaceutical composition as claimed in claim 2, which is an antidiabetic drug.

4. A pharmaceutical composition as claimed in claim 2, which is an antilipemic drug.

5. A method for treating obesity, comprising administering a fructose-6-phosphate-2-kinase inhibitor.

6. A method for treating diabetes, comprising administering a fructose-6-phosphate-2-kinase inhibitor.

7. A method for treating hyperlipidemia, comprising administering a fructose-6-phosphate-2-kinase inhibitor.

8. A method as claimed in claim 5, wherein the fructose-6-phosphate-2-kinase inhibitor is itaconic acid or a salt thereof.

9. A method as claimed in claim 5, wherein the fructose-6-phosphate-2-kinase inhibitor is itaconic acid or a salt thereof.

10. A method as claimed in claim 6, wherein the fructose-6-phosphate-2-kinase inhibitor is itaconic acid or a salt thereof.

* * * * *